(12) United States Patent
Kevil et al.

(10) Patent No.: US 10,254,262 B2
(45) Date of Patent: Apr. 9, 2019

(54) HYDROGEN SULFIDE DETECTING APPARATUS

(71) Applicants: Board of Supervisors of Louisiana State University and Agricultural and Mechanical College, Baton Rouge, LA (US); Louisiana Tech University, Ruston, LA (US)

(72) Inventors: Christopher G. Kevil, Shreveport, LA (US); John D. Glawe, Benton, LA (US); Clifton F. Frilot, Haughton, LA (US); Leland Weiss, Ruston, LA (US)

(73) Assignees: Board of Supervisors of Louisiana State University and Agricultural and Mechanical College, Baton Rouge, LA (US); Louisiana Tech University, Ruston, LA (US)

( * ) Notice: Subject to any disclaimer, the term of this patent is extended or adjusted under 35 U.S.C. 154(b) by 0 days.

(21) Appl. No.: 14/780,799

(22) PCT Filed: Mar. 28, 2014

(86) PCT No.: PCT/US2014/032173
§ 371 (c)(1),
(2) Date: Sep. 28, 2015

(87) PCT Pub. No.: WO2014/160937
PCT Pub. Date: Oct. 2, 2014

(65) Prior Publication Data
US 2016/0041139 A1 Feb. 11, 2016

Related U.S. Application Data

(60) Provisional application No. 61/806,017, filed on Mar. 28, 2013.

(51) Int. Cl.
*G01N 33/00* (2006.01)
*G01N 27/40* (2006.01)
(Continued)

(52) U.S. Cl.
CPC ..... *G01N 33/0044* (2013.01); *G01N 33/0013* (2013.01); *G01N 27/40* (2013.01); *G01N 31/223* (2013.01); *G01N 33/4925* (2013.01)

(58) Field of Classification Search
None
See application file for complete search history.

(56) References Cited

U.S. PATENT DOCUMENTS 7,282,081 B2 10/2007 Verscharen
7,923,037 B2 4/2011 Tomaselli et al.
(Continued)

FOREIGN PATENT DOCUMENTS

EP 0584568 A1 3/1994
WO 01/63094 A1 8/2001
(Continued)

OTHER PUBLICATIONS

Levitt, M. D. et al., Free and Acid-Labile Hydrogen Sulfide Concentrations in Mouse Tissues: Anomalously High Free Hydrogen Sulfide in Aortic Tissue, 2011, Antioxidants & Redox Signaling, vol. 15(2), pp. 373-378.*
(Continued)

*Primary Examiner* — Xiaoyun R Xu
(74) *Attorney, Agent, or Firm* — Davis & Bujold, PLLC; Charles G. Holoubek

(57) ABSTRACT

A hydrogen sulfide ($H_2S$) detecting apparatus for measuring the concentrations of hydrogen sulfide species in a given sample is disclosed. The hydrogen sulfide detecting apparatus can comprise a plurality of reaction chambers separated from a plurality of trapping chambers by a ($H_2S$)
(Continued)

permeable membrane, with the reaction chambers and trapping chambers each having buffer component(s) and/or reactive agents that expose the incoming sample to a particular pH and chemical environment in order to allow for the selective liberation and trapping of hydrogen sulfide from the sample.

18 Claims, 7 Drawing Sheets

(51) Int. Cl.
 *G01N 31/22* (2006.01)
 *G01N 33/49* (2006.01)

(56) References Cited

U.S. PATENT DOCUMENTS

| | | | |
|---|---|---|---|
| 7,959,864 | B2 | 6/2011 | Jiang et al. |
| 8,268,146 | B2 | 9/2012 | Jiang et al. |
| 2009/0184005 | A1* | 7/2009 | Zhang ............... G01N 27/4045 205/786.5 |
| 2012/0073988 | A1 | 3/2012 | Zhang et al. |
| 2014/0291168 | A1* | 10/2014 | Li ..................... G01N 27/4161 205/778.5 |

FOREIGN PATENT DOCUMENTS

| | | |
|---|---|---|
| WO | 2010/102279 A1 | 9/2010 |
| WO | 2012/125723 A3 | 9/2012 |

OTHER PUBLICATIONS

Sawula, W. et al., Improved HPLC method for total plasma homocysteine detection and quantification, 2008, Acta Biochimica Polonica, vol. 55(1), pp. 119-125.*

Nguyen, N-T, et a. Micromachined polymer electrolyte membrane and direct methanol fuel cells—a review, 2006, Journal of Micromechanics and Microengeering, vol. 16, pp. R1-12.*

Zhang, Y. et al. Multiple Gene Analysis Within a Simple Droplet-In-Oil Microfluidic PCR Platform, Twelfth International Conference on Miniaturized Systems for Chemistry and Life Sciences Oct. 12-16, 2008, San Diego, California, USA.*

PCT WO2014/160937 A1, Publication with Search Report, Oct. 2, 2014.

PCT/US2014/032173, International Preliminary Report on Patentability, Sep. 29, 2015.

X. Shen et al., "Analytical measurement of discrete hydrogen sulfide pools in biological specimens", Free Radical Biology and Medicine, Elsevier Inc., US, vol. 52, No. 11, pp. 2276-2283, Apr. 6, 2012.

European Search Report corresponding to EP 14 77 2704 completed on Sep. 7, 2016.

Response to Examiner's Report for Australian Patent App. No. 2014240947, dated Mar. 19, 2018.

Notice of Acceptance for Australian Patent App. No. 2014240947, dated Mar. 29, 2018.

Response Office Action in Canadian Patent App. No. 2,907,896, dated Mar. 1, 2018.

Official Action for Canadian Patent App. No. 2,907,896, finding only defect in application is incorporation by reference, dated Aug. 2, 2018.

Official Action for Chilean Patent App. No. 201502895, finding claims as filed novel and inventive (see pp. 7-13).

Notice of decision to grant European Patent Application No. 14772704.4 (now EP 2,979,086) dated May 31, 2017.

Notice of decision to grant Mexican Patent Application No. 2015013571 (now MX 350580) dated Jun. 29, 2018, with claims originally rejected based on Zhang et al. '005, after response similar to Australian Patent App, claims were allowed substantially as originally filed (no translation available).

* cited by examiner

Representative working chamber conditions and electrochemical detection

Diffusion of $H_2S$ across different thickness PDMS and fluorescence detection by HPLC, showing transfer efficiency of $H_2S$ gas transfer from the acid reaction chamber into the trapping chamber as measured using MBB detector.

HYDROGEN SULFIDE DETECTING APPARATUS

I. CROSS-REFERENCE TO RELATED APPLICATION

This application claims the benefit of U.S. Provisional Application No. 61/806,017, filed Mar. 28, 2013, which is hereby incorporated by reference.

II. THE NAMES OF THE PARTIES TO A JOINT RESEARCH AGREEMENT

The claimed invention was made by, on behalf of, and/or in connection with the following parties to a joint university corporation research agreement: Louisiana Tech University and the Board of Supervisors of Louisiana State University and Agricultural and Mechanical College. The agreement was in effect on and before the date the claimed invention was made, and the claimed invention was made as a result of activities undertaken within the scope of the agreement.

III. FIELD OF THE INVENTION

The present invention relates to a novel apparatus and methods for the measurement of hydrogen sulfide in its various bioavailable forms.

IV. BACKGROUND OF THE INVENTION

Hydrogen sulfide ($H_2S$) is a colorless gasotransmitter (gaseous signaling molecule) that plays a vital role in numerous cellular functions within the human body. For instance, over the past decade, the role of $H_2S$ beyond a toxicant and environmental pollutant has evolved to encompass several biochemical functions that are important in various physiological and pathological responses such as cardiovascular (dys)function, neurological (dys)function, gastrointestinal (dys)function, immune (dys)function, and several other molecular and cell biology responses.

For instance, $H_2S$ has been discovered to have significant potential to contribute to the detection and treatment of cardiovascular disease, including atherosclerosis and peripheral arterial disease. Because of decreased oxidative modification of low-density lipoprotein (LDL), $H_2S$ has also been shown to play a significant role in atherosclerosis by having noted effects on monocyte recruitment, transformation into tissue macrophages, and foam cell formation. Further, $H_2S$ has been shown to inhibit hypochlorite and hemin-mediated atherogenic modification of LDL. Plasma $H_2S$ levels have also been shown to be lower in atherosclerotic plaque, and treatment with sodium hydrosulfide (NaHS) decreases both aortic plaque and intercellular adhesion molecule-1 (ICAM-1). In addition, $H_2S$ down regulates the expression of monocyte chemoattractant protein-1, a CC chemokine that binds to the C—C chemokine receptor type 2 (CCR2) and recruits monocytes into the subendothelial layer to form atherosclerotic plaque. Another critical role of $H_2S$ in the pathogenesis of atherosclerosis is the effect of inducing apoptosis on vascular smooth muscle cells, which generates atherosclerotic plaque. Hydrogen sulfide, administered as NaHS, decreases the proliferation of vascular smooth muscle cell via a mitogen-activated protein kinase (MAPK) pathway in a dose-dependent fashion in rat models. Additional work with a rat model reveals that $H_2S$ reduced vascular calcification. Additionally, recent studies have shown $H_2S$ to have a direct relationship with nitrogen monoxide and carbon monoxide in peripheral arterial disease (PAD) identification.

Hydrogen sulfide arises from multiple biological sources and tissues (e.g. bacteria and organ-specific production). Endogenous biological $H_2S$ production primarily originates from cysteine metabolism through the activity of cystathionine β-synthase and cystathione γ-lyase or through 3-mercaptopyruvate metabolism by 3-mercaptosulfurtransferase. $H_2S$ can come from redox-dependent metabolism of polysulfides involving glutathione or other small molecular weight thiol modifiers. Lastly, $H_2S$ also arises from different environmental sources that affect humans such as petroleum production and exploration, food and beverage processing, waste disposal and sewage treatment, agriculture and farming, and bacterial contamination and function.

Hydrogen sulfide chemistry is complex and plays several roles in modulating protein thiol function. It affects numerous biological responses involving signal transduction responses, mitochondrial respiration, gene expression, and cell survival/viability. At a physiological pH of ~7.2-7.4, $H_2S$ predominantly (~80%) exists in its anion $HS^-$ form with a smaller amount in the gaseous $H_2S$ form (~20%). This is due to pKa regulation of $H_2S$ forms in aqueous solutions as illustrated in the following equation:

$$pKa_1 = 7.04 \quad pKa_2 \geq 13$$

$$H_2S \leftrightarrows HS^- \leftrightarrows S^{2-}$$

Due to the different pKa's, the ionic distribution is easily manipulated and, in turn, its distribution controlled in either aqueous or gas phases.

Hydrogen sulfide is very reactive within biological or environmental systems, resulting in sulfide equivalents being present in three different volatile sulfur pools as shown in FIG. 1. These three pools—free $H_2S$, acid labile $H_2S$, and sulfane sulfur species—are important in regulating the amount of bioavailable sulfur. Free hydrogen sulfide is found dissolved in plasma and other tissue fluids. At mammalian body conditions (i.e., pH 7.4 and temperature of 37° C.), 18.5% of free hydrogen sulfide exists as $H_2S$ gas, and the remainder is almost all hydrosulfide anion (HS−) with a negligible contribution of $S^{2-}$. Sulfane sulfur refers to divalent sulfur atoms bound to another sulfur, though they may bear an ionizable hydrogen at some pH values. Examples of these bound sulfurs include thiosulfate $S_2O_3^{2-}$, persulfides R—S—SH, thiosulfaonates R—S(O)—S—R', polysulfides R—$S_n$—R, polythionates $S_nO_6^{2-}$, and elemental sulfur $S^0$. Acid labile sulfide, the other major bioavailable pool, consists of sulfur present in iron-sulfur clusters contained in iron-sulfur proteins (non-heme), which are ubiquitous in living organisms, and include a variety of proteins and enzymes, including without limitation, rubredoxins, ferredoxins, aconitase, and succinate dehydrogenase. The acid labile sulfides readily liberate free $H_2S$ in acid conditions (pH<5.4), and the process of acid liberation may also release hydrogen sulfide from persulfides, which have traditionally been classified as sulfane sulfur. This acid labile sulfur pool has been postulated to be a reversible sulfide sink and may be an important storage pool that regulates the amount of bioavailable free hydrogen sulfide.

$H_2S$ equivalents are readily mobilized from these pools based on changes in pH, $O_2$ concentration, and oxidative/reductive chemistry that affect biological and biochemical responses. Thus, detection of $H_2S$ availability from these distinct pools is important for clinical pathophysiology diagnosis, environmental source identification, and any other organic or inorganic chemistry uses.

Unfortunately, a significant barrier to the study of hydrogen sulfide's role in human health and disease has been the lack of precise methodology and testing means for the accurate and reproducible measurement of hydrogen sulfide both in vivo and in vitro. A variety of methods to measure free $H_2S$ have been employed, but with divergent results. These methods include a spectrophotometric derivatization method resulting in methylene blue formation, variations of this methylene blue method using high performance liquid chromatography, sulfide ion-selective electrodes, polarographic sensors, gas chromatography, and high-performance liquid chromatography (HPLC) in conjunction with fluorimetric based methods using monobromobimane (MBB) to derivatize free $H_2S$. The complexity of analytical $H_2S$ measurement, especially in living organisms, reflects the fact that hydrogen sulfide is a reactive gas and exists in the organism in the three different volatile sulfur pools shown in FIG. 1. Due to a lack of reliable, accurate analytical detection methods available to quantify $H_2S$ and its various forms, there is great disagreement regarding precise amounts and sources of $H_2S$ metabolism in biological and biochemical settings. Therefore, there is a great need for an apparatus and associated methodology that can be used to accurately and conveniently measure $H_2S$ in its various bioavailable forms.

V. SUMMARY OF THE INVENTION

The invention disclosed herein is directed to a hydrogen sulfide ($H_2S$) detecting apparatus for measuring the concentrations of hydrogen sulfide species in a given sample. In a particular embodiment exemplifying the principles of the invention, the hydrogen sulfide detecting apparatus can comprise a plurality of reaction chambers separated from a plurality of trapping chambers by a $H_2S$ permeable membrane, with the reaction chambers and trapping chambers each having buffer component(s) and/or reactive agents that expose the incoming sample to a particular pH and chemical environment in order to allow for the selective liberation and trapping of hydrogen sulfide from the sample.

In a preferred embodiment, the $H_2S$ detecting apparatus features three reaction chambers, namely: a free sulfide reaction chamber having a pH from about 7.0 to about 7.5; an acid labile sulfide reaction chamber having a pH from about 2.6 to about 6.0; and a total sulfide reaction chamber having a pH from about 2.6 to about 6.0 and a reducing agent. Three corresponding trapping chambers can be positioned adjacent to the plurality of reaction chambers such that $H_2S$ gas released from the reaction chambers will diffuse across the $H_2S$-permeable membrane and into the corresponding trapping chamber. The trapping chambers each have an alkaline environment with a pH from about 9.5 to about 10.0 in order to re-dissolve and trap the hydrogen sulfide gas. Detection can then be accomplished by one of the three following methods: (a) electrochemical, (b) fluorescence, or (c) colorimetric.

The $H_2S$ detecting apparatus of the present invention can also feature a cap, an injection chamber, and a base. The cap can be positioned adjacent to the injection chamber to allow a test sample to be injected through the cap and into the injection chamber. The injection chambers can be in fluid communication with the reaction chambers via a plurality of inlets. The base can be positioned adjacent to the plurality of trapping chambers. The base can be transparent to enable fluorimetric or colorimetric detection of $H_2S$ in the adjacent trapping chambers. The base can also feature a plurality of electrode systems to enable electrochemical detection of $H_2S$ in the adjacent trapping chambers.

The $H_2S$ detecting apparatus of the present invention enables the simultaneously detection of free $H_2S$, acid labile amounts of $H_2S$, bound sulfane sulfur available $H_2S$, and overall total bioavailable $H_2S$ from a single test sample. The concentration of $H_2S$ in the various pools can be calculated as follows: the free $H_2S$ and total $H_2S$ concentrations will be equal to the detected concentrations in the free sulfide trapping chamber and total sulfide trapping chamber, respectively. The acid labile $H_2S$ amount can be determined by subtracting the amount measured in the free sulfide trapping chamber from that of the acid labile sulfide trapping chamber. Lastly, the bound $H_2S$ concentration can be determined by subtracting the acid labile trapping chamber concentration from the total sulfide trapping chamber concentration.

The above summary is not intended to describe each illustrated embodiment or every possible implementation. These and other features, aspects, and advantages of the present invention will become better understood with regard to the following description, appended claims, and accompanying drawings.

VI. BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages in accordance with the present invention:

Figure 1:
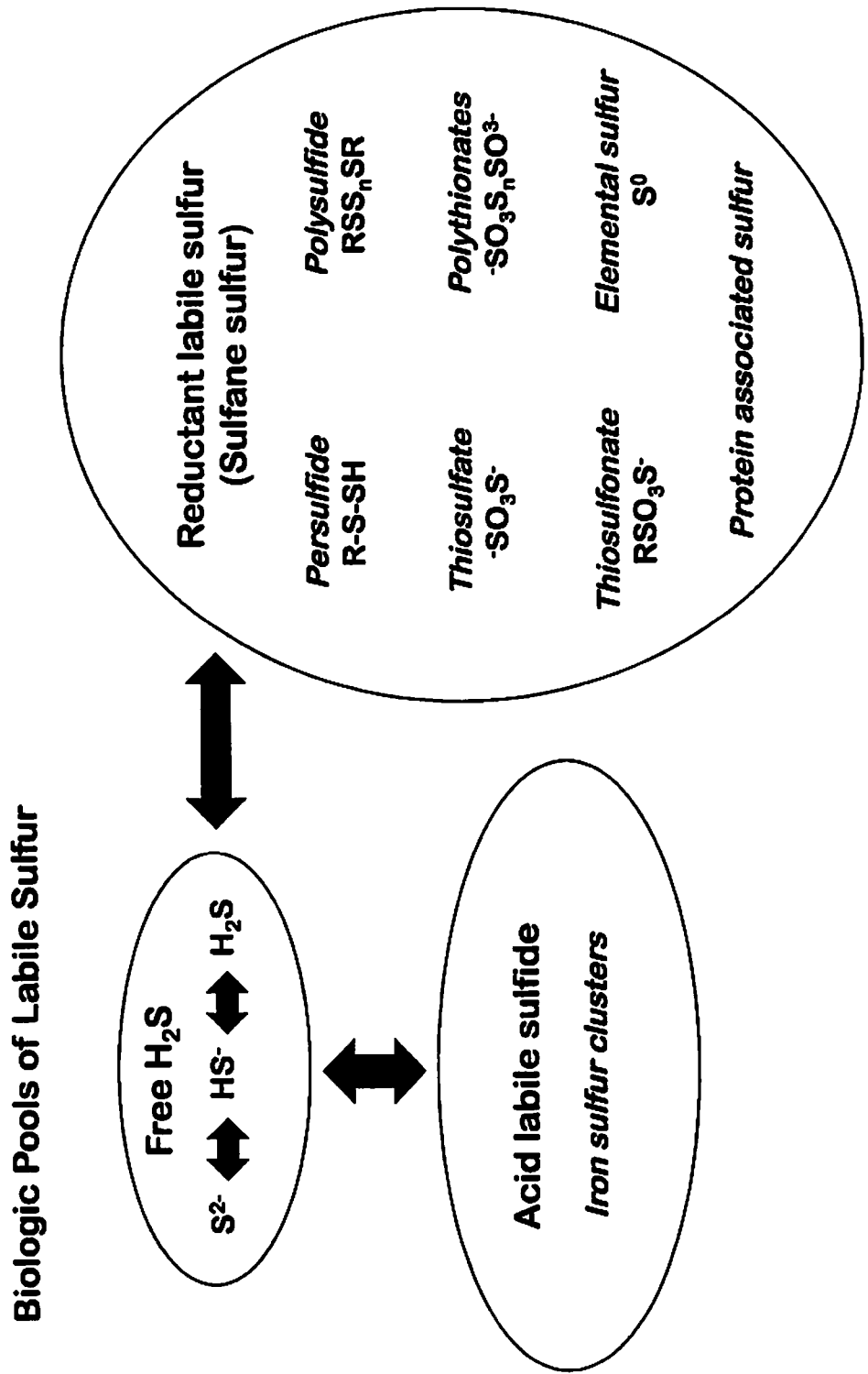
FIG. 1 illustrates the three biological pools of sulfide found in organisms.
Figure 2:
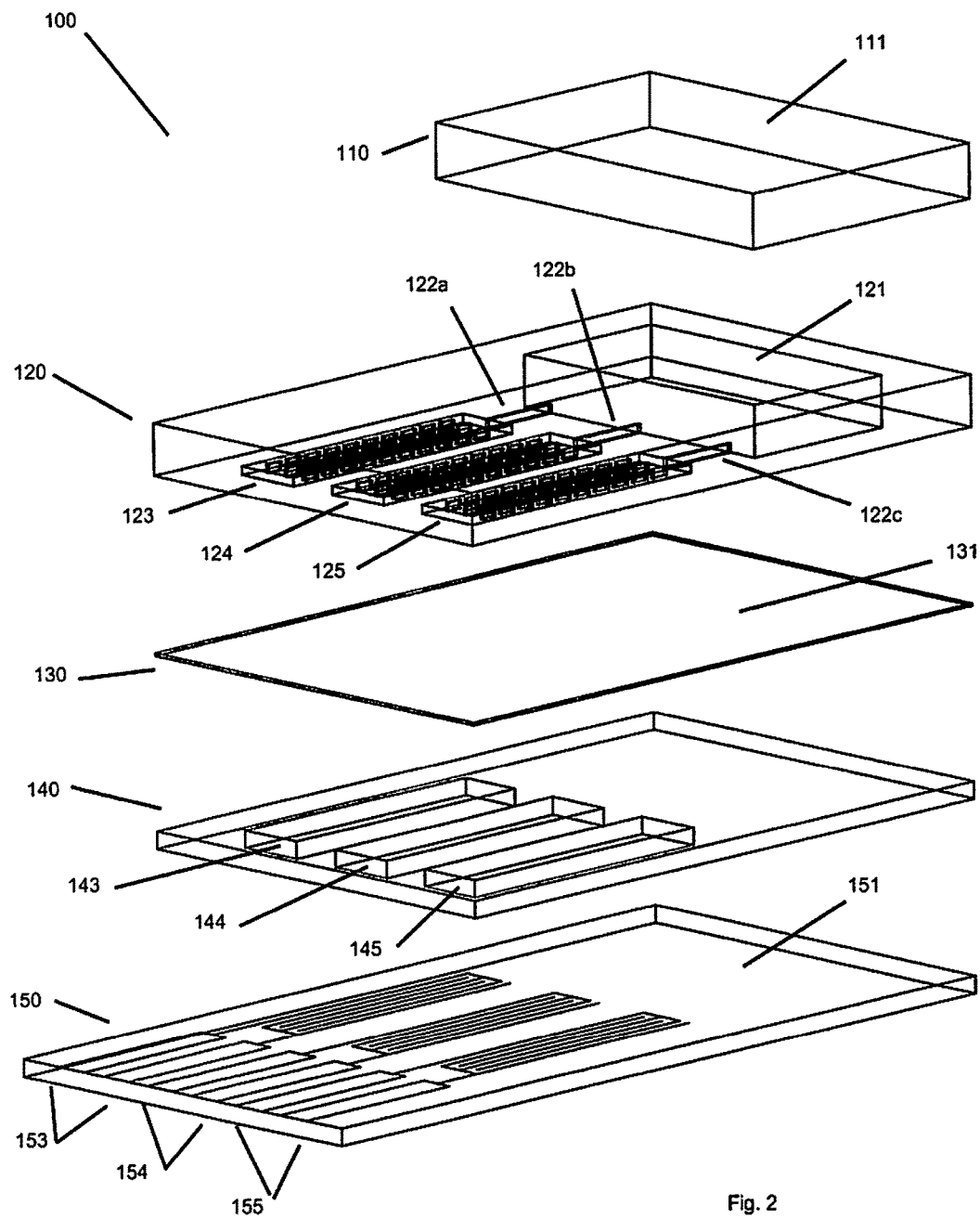
FIG. 2 is an exploded view of an embodiment of a hydrogen sulfide detecting apparatus exemplifying the principles of the present invention.
Figure 5:
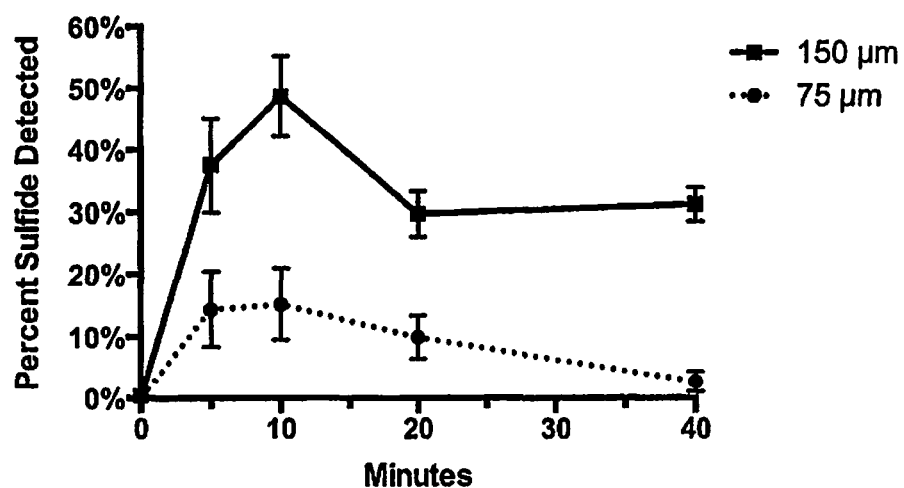

FIG. 5 illustrates the diffusion of hydrogen sulfide across a polydimethyl-siloxane (PDMS) membrane of different thicknesses, showing the transfer efficiency of hydrogen sulfide gas transfer from the reaction chambers to the trapping chambers of the hydrogen sulfide detecting apparatus depicted in FIG. 2. The transfer efficiency was measured with high-performance liquid chromatography (HPLC) in conjunction with fluorimetric based methods using monobromobimane (MBB) to derivatize free $H_2S$.

Figure 6:
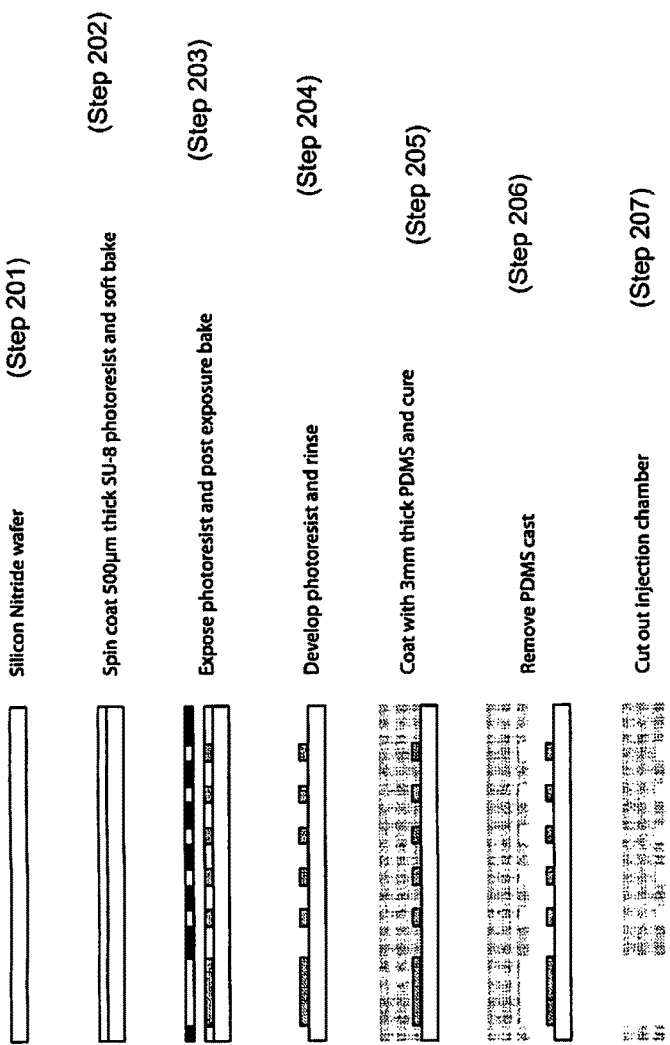

FIG. 6 illustrates an embodiment of a manufacturing process for the creation of a hydrogen sulfide detecting apparatus exemplifying the principles of the present invention.

Figure 7:
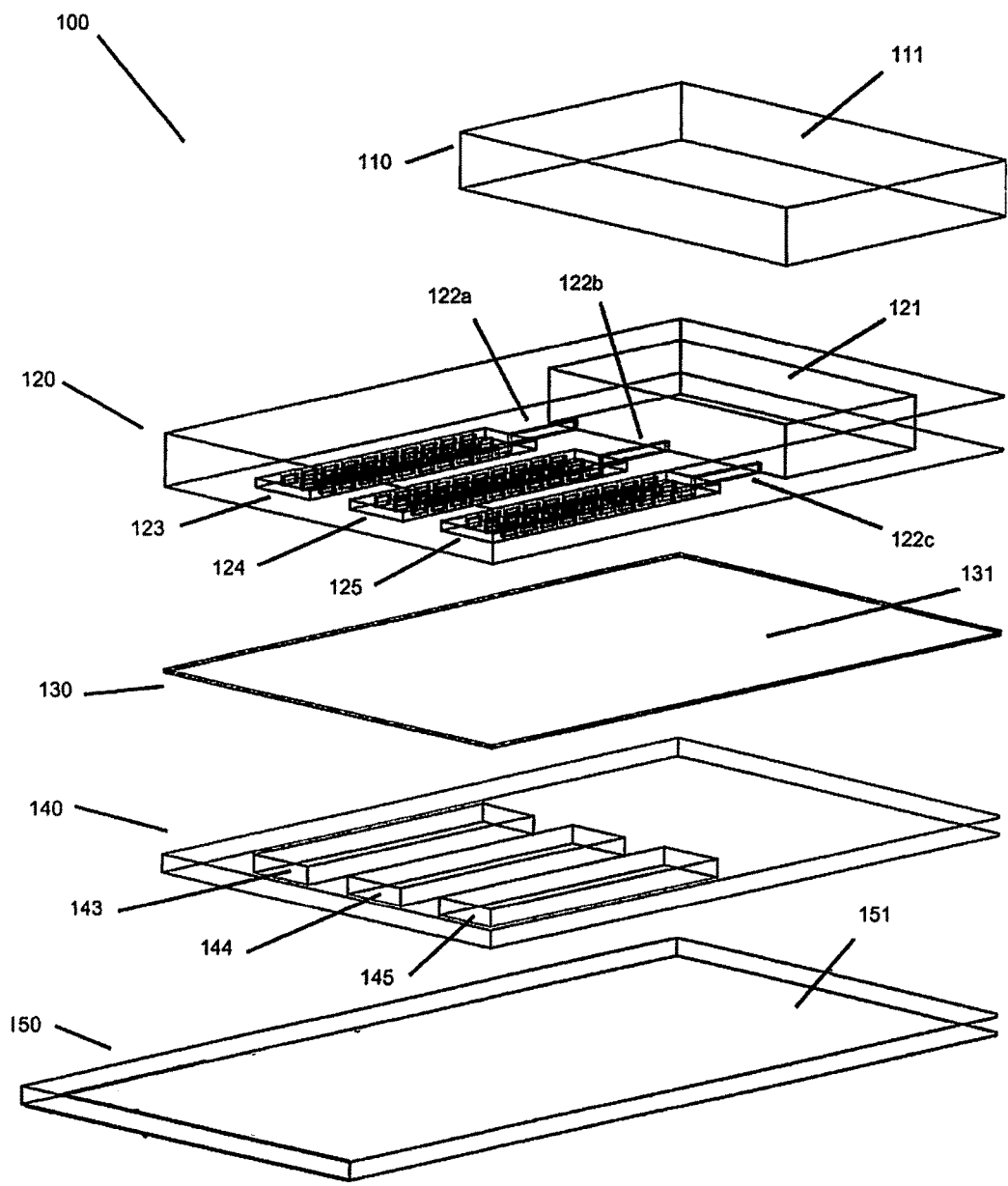

FIG. 7 is an exploded view of an alternative embodiment of a hydrogen sulfide detecting apparatus exemplifying the principles of the present invention.

VII. DETAILED DESCRIPTION OF THE INVENTION

Detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Alternate embodiments may be devised without departing from the spirit or the scope of the invention. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward.

As used herein, the terms "a" or "an" are defined as one or more than one. The term "plurality," as used herein, is defined as two or more than two. The term "another," as used herein, is defined as at least a second or more. The terms "comprises," "comprising," or any other variation thereof are intended to cover a non-exclusive inclusion, such that a process, method, article, or apparatus that comprises a list of elements does not include only those elements, but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including," "having," or "featuring," as used herein, are defined as comprising (i.e., open language). The term "coupled," as used herein, is defined as connected, although not necessarily directly, and not necessarily mechanically. As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. Relational terms such as first and second, top and bottom, right and left, and the like may be used solely to distinguish one entity or action from another entity or action without necessarily requiring or implying any actual such relationship or order between such entities or actions.

As used herein, the abbreviation CA refers to chronoamperometry; the abbreviation DPV refers to differential pulse voltammetry; the abbreviation DTPA refers to diethylenetriamine pentaacetate; the abbreviation HPLC refers to high-performance liquid chromatography; the abbreviation PCR refers to polymerase chain reaction; and the abbreviation PDMS refers to polydimethyl-siloxane.

Herein various embodiments of the present invention are described. To avoid redundancy, repetitive description of similar features may not be made in some circumstances.

Figure 3:
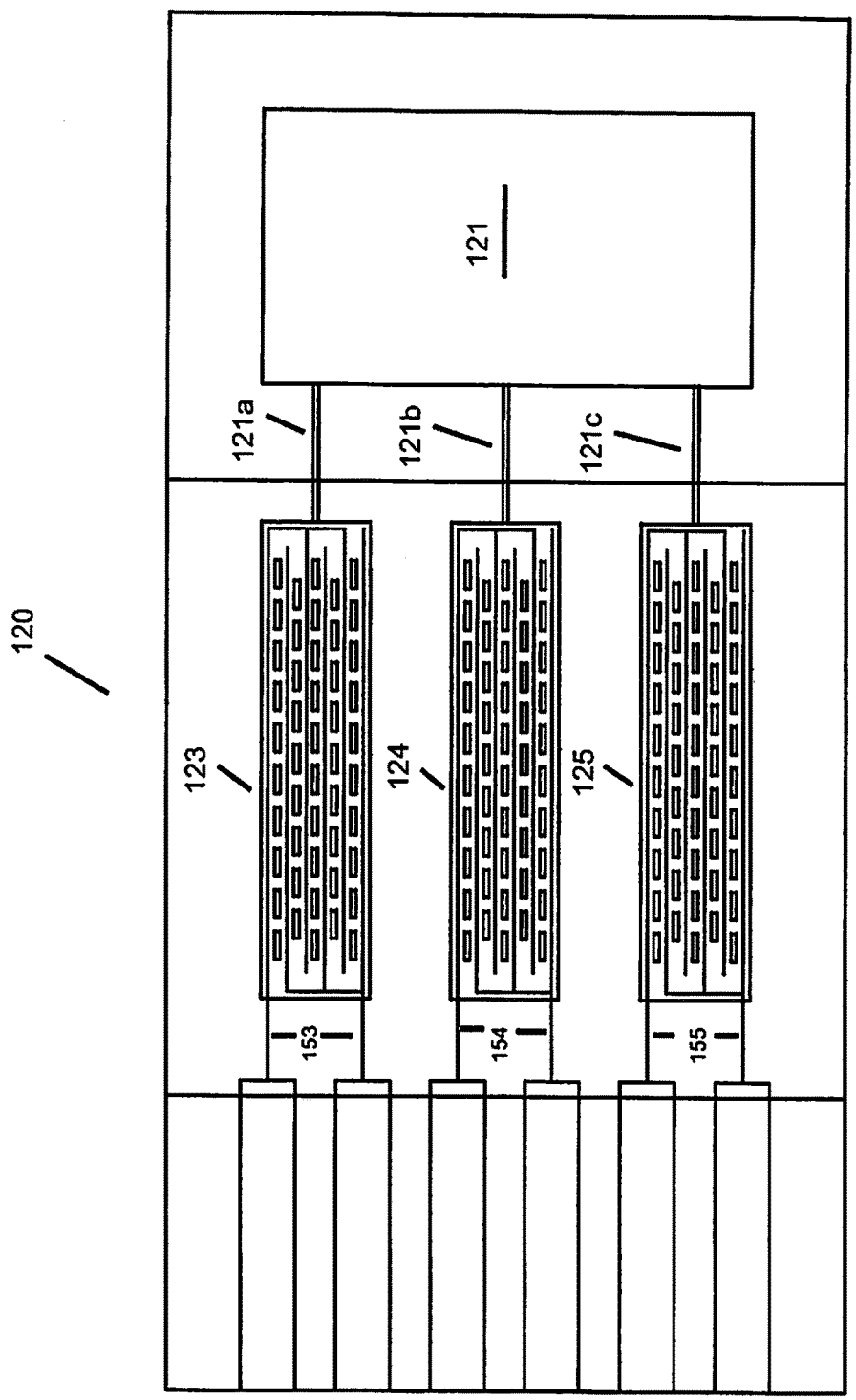
FIG. 3 is a top view of an embodiment of the reaction chamber of the hydrogen sulfide detecting apparatus depicted in FIG. 2.

An embodiment of a hydrogen sulfide detecting apparatus exemplifying the principles of the present invention is shown in FIGS. 2 and 3. The apparatus 100 is a lab-on-a-chip device that allows $H_2S$ in its various bioavailable forms to be measured in a reliable, analytical fashion employing unique reaction chemistry, micro-manufacturing techniques, and selective electrochemical measurement techniques. In particular, the apparatus 100 allows for rapid measurement of $H_2S$ from the free $H_2S$, acid labile sulfide, and sulfane sulfur (polysulfide/persulfide) pools by featuring at least three reaction chambers each having a particular pH and reaction chemicals present to allow for the selective liberation and trapping of $H_2S$ from these pools. The apparatus 100 can be used for research, environmental, and clinical diagnostic purposes in determining hydrogen sulfide bioavailability in biological or other samples. The apparatus 100 is particularly useful for the detection of $H_2S$ in plasma or any other biological or liquid sample. In a preferred embodiment, the apparatus 100 is designed for a single use; however, the apparatus 100 could be configured to be reusable in other embodiments.

Still referring to FIGS. 2 and 3, an embodiment of the hydrogen sulfide detecting apparatus 100 can comprise: a cap 111; an injection chamber 121; a plurality of reaction chambers 123, 124, 125; a permeable membrane 131; a plurality of trapping chambers 143, 144, 145; and a base 151. The cap 111 is preferably constructed out of butyl rubber and is positioned adjacent to the injection chamber 121 to allow a test sample to be injected through the cap 111 and into the injection chamber 121. The injection chamber 121 is in fluid communication with the reaction chambers 123, 124, 125 via inlet channels 122a-c. The permeable membrane 131 separates the reaction chambers 123, 124, 125 from adjacent trapping chambers 143, 144, 145. The trapping chambers 143, 144, 145 are positioned adjacent to electrode systems 153, 154, 155 on the base 151.

In a preferred embodiment, the injection chamber 121 comprises a single piece PDMS-molded (polydimethylsiloxane) chamber which is evacuated of air and adapted to receive fluid injected directly into it. A first inlet channel 122a connects the injection chamber 121 to free sulfide reaction chamber 123; a second inlet channel 122b connects the injection chamber 121 to the acid labile sulfide reaction chamber 124; and a third inlet channel 122c connects the injection chamber 121 to the total sulfide-reaction chamber 125. In this arrangement, the reaction chambers 123, 124, 125 are reproducibly filled with uniform volumes from a single injection while minimizing diffusion of buffer components and reaction products between the chambers.

Figure 4:
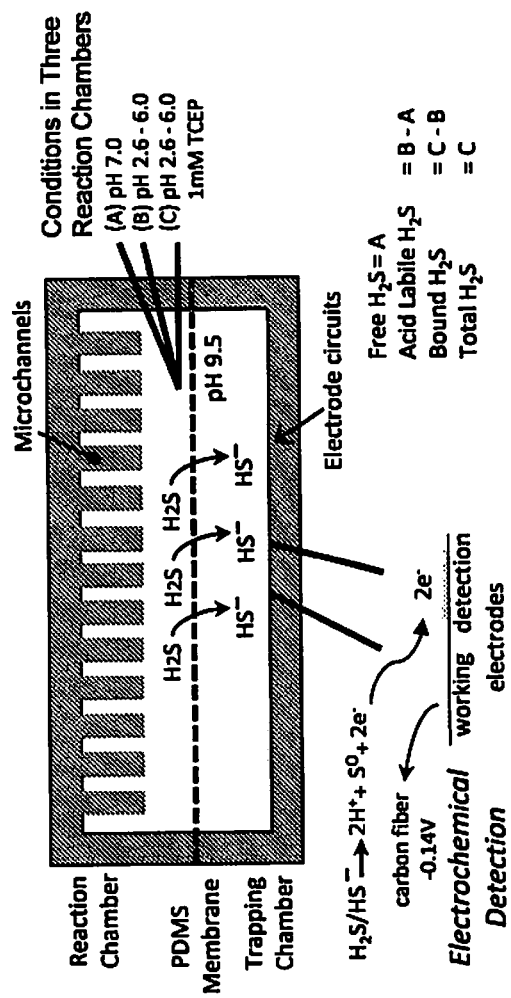
FIG. 4 illustrates representative reaction chamber conditions and the electrochemical detection methodology employed by a hydrogen sulfide detecting apparatus exemplifying the principles of the present invention.

Each reaction chamber 123, 124, and 125 preferably comprises interdigitated microchannels of PDMS with dried or powder-coated buffer components and/or reactive agents that expose the incoming sample to a particular pH and chemical environment in order to allow for the selective liberation and trapping of hydrogen sulfide. FIG. 4 illustrates representative reaction chamber conditions of the hydrogen sulfide detecting apparatus 100. Free or volatilized hydrogen sulfide is derivatized in alkaline conditions, preferably pH>7.0. The derivatization preferably occurs under low oxygen conditions, preferably <5% oxygen, more preferably <2% oxygen, and most preferably ≤1% oxygen. Accordingly, in a preferred embodiment, the free sulfide-reaction chamber 123 is at neutral pH environment (pH from about 7.0 to about 7.5). Meanwhile, the release of hydrogen sulfide from the acid labile pool generally requires a pH less than 5.4. Thus the determination of acid labile sulfide involves acidification of the sample, preferably pH <4.0, more preferably from about pH 2.0 to about pH 3.0, and most preferably about pH 2.6, thereby causing release of free hydrogen sulfide from the acid labile pool. Accordingly, the acid labile sulfide-reaction chamber 124 is preferably at an acid pH environment (pH from about 2.6 to about 6.0). Lastly, the total sulfide-reaction chamber 125 is preferably at an acidic pH environment (pH from about 2.6 to about 6.0) with a reducing agent present such as 1 mM tris (2-carboxyethyl) phosphine hydrochloride (TCEP). The total labile sulfide amount, including the sulfane sulfur component along with the acid-labile and free sulfide, is determined by using a reducing agent with an acid solution. The reducing agent is preferably TCEP, which cleaves disulfide bonds to liberate the sulfane sulfur atom. While dithiothreitol (DTT) could also be used, TCEP is preferred because it is water soluble, non-volatile, reduces disulfide bonds more rapidly and has been shown to be very stable across a wider range of pH (2.0-9.5) than DTT. TCEP does not have a thiol moiety and has the additional advantage of not requiring thiol removal prior to reaction with MBB. By contrast DTT contains a thiol moiety and has been reported to have small amounts of sulfide contaminants.

The permeable membrane 131 is positioned between the reaction chambers 123, 124, 125 and the corresponding trapping chambers 143, 144, 145. The $H_2S$ permeable membrane 131 is preferably silicone-based or may comprise blended materials such as silicone-polycarbonate blends. The thickness of the $H_2S$ permeable membrane 131 may vary between about 75 μm to about 500 μm or greater depending on device construction, application, and required mechanical strength. Other constructions may utilize membrane materials that include silicone and additive compounds for increased specificity of hydrogen-sulfide permeability. These include, but are not limited to, the combination of silicone and polycarbonate for membranes or dimethyl silicone. Other membrane base materials may be utilized which include but are not limited to composite membranes with silicone or PDMS coating on micro-porous cellulose structure. Membrane fabrication may be completed via microfabrication or other techniques. Preferential techniques include spinning membrane polymer in liquid form onto a flat surface like a silicon-nitride wafer. The membrane may be subsequently released following curing, the removal of entrapped air bubbles and solidification. Other techniques include but are not limited to Reactive Ion Etch (RIE) processes. This includes the deposition of the liquid polymer membrane atop a wafer, and then patterning and removing the wafer substrate to release the membrane for use.

The trapping chambers 143, 144, 145 are positioned beneath the reaction chambers 123, 124, 125 such that $H_2S$ gas released from each reaction chamber will diffuse across the permeable membrane 131 and into the corresponding trapping chamber. All three trapping chambers 143, 144, 145 are filled with an alkaline solution (100 mM NaOH, pH from about 9.5 to about 10) to trap and re-dissolve the hydrogen sulfide gas which diffuses across the permeable membrane 131. In a preferred embodiment, the trapping chambers are constructed out of PDMS. However, other materials and construction processes may be utilized, including but not limited to solid casting, RIE patterning of silicon, and 3-D printing of non-porous chambers using 3-D printing material.

The base 151 is preferably constructed out of plastic. However, it may be constructed out of other base materials including but not limited to silicon, silicon nitride, or metallic materials. In the embodiment depicted in FIGS. 2 and 3, the base 151 features interdigitated electrode systems 153, 154, 155 for electrochemical detection of $H_2S$ in the adjacent trapping chambers 143, 144, 145. The electrode systems 153, 154, 155 can each feature a working electrode, a counter electrode, and a reference electrode. The working electrodes can be constructed out of inert metals such as gold, silver or platinum, are preferably medical grade carbon fibers (6 μm diameter; 12 Ω-cm). Other embodiments may include use of graphene or similar thin-sheet materials for electrode application. The working electrodes can be fixed in the base 151 longitudinally so as to allow exposure to the sample in the trapping chambers 143, 144, 145. The counter electrode is preferably constructed out of an electrochemically inert material such as gold, platinum, or carbon and can be fixed in the base 151 parallel to the working electrode (preferably with 1 mm-5 mm separation) in order to detect electrons produced by the oxidation reaction occurring in the trapping chambers 143, 144, 145. The reference electrode is preferably constructed out of platinum or Ag/AgCl wire in electrical contact with the specimen. Alternatively, and as depicted in FIG. 7, the base 151 can be constructed out of a transparent material (e.g., plastic) to allow $H_2S$ levels in the trapping chambers 143, 144, 145 to be detected via fluorescence, chemiluminescence and colorimetric detection. In another alternative embodiment, the base 151 can be constructed out of a transparent material while also featuring electrode systems, thereby providing a user the option of detection methods.

In operation, a sample can be deposited into the injection chamber 121 by using a needle to penetrate the cap 111. The sample will be transmitted in uniform volumes to the free sulfide reaction chamber 123, the acid labile sulfide reaction chamber 124, and the total sulfide-reaction chamber 125 via the first inlet channel 122a, the second inlet channel 122b, and the third inlet channel 122c, respectively. The releasing chambers 123, 124, 125 are separated from their corresponding trapping chambers 143, 144, 145 by the $H_2S$ permeable membrane 131. In the free sulfide-reaction chamber 123, only free $H_2S$ gas will diffuse across the membrane 131 into the free sulfide trapping chamber 143. In the acid labile sulfide-reaction chamber 124, both the free $H_2S$ and acid labile $H_2S$ pools will diffuse across the membrane 131 into the acid labile sulfide trapping chamber 144. In the total sulfide-reaction chamber 125, $H_2S$ from all three pools (free, acid labile, and bound sulfane sulfur) are released and will diffuse into the corresponding total sulfide trapping chamber 145. Upon entry into the trapping chambers 143, 144, 145, the $H_2S$ is converted from its gaseous form into the $HS^-$ form due to the presence of basic (pH ~9.5-10.0) conditions. The concentration of $H_2S$ in the various pools then can be calculated as follows: the free $H_2S$ and total $H_2S$ concentrations is equal to that measured by the free sulfide trapping chamber 143 and total sulfide trapping chamber 145, respectively. The acid labile $H_2S$ amount is determined by subtracting the amount measured in the free sulfide trapping chamber 143 from that of the acid labile sulfide trapping chamber 144. The bound $H_2S$ concentration is determined by subtracting the acid labile trapping chamber 144 concentration from the total sulfide trapping chamber 145 concentration. In this way, the device simultaneously detects free $H_2S$, acid labile amounts of $H_2S$, bound sulfane sulfur available $H_2S$, and overall total bioavailable $H_2S$ from one specimen.

Electrochemical Detection

As depicted in FIGS. 2 and 4, the hydrogen sulfide detecting apparatus 100 can feature a base 151 having integrated electrode systems 153, 154, 155 for the electrochemical detection of $H_2S$ in the trapping chambers 143, 144, 145. Contemporary electrochemical methods used for in vivo and in vitro detection of biological compounds are chronoamperometry (CA) and differential pulse voltammetry (DPV). Both CA and DPV utilize a three-electrode system (reference, counter and working). In CA, the working electrode potential is held constant (with respect to the reference electrode) and current is measured as a function of time. Excellent temporal resolution and sensitivity is achieved with this technique. However, the origin of the current cannot be discriminated, for the measured current is a superposition of any species that is electrolyzed at or below the working electrode potential. For single species concentration determination, selective working electrodes must be used.

DPV is a hybrid of traditional cyclic voltammetry and CA. The sensitivity is similar to CA, but the temporal resolution is less. DPV has a potential applied to the working electrode that is a linearly increasing pulse train. The difference in current per pulse is recorded as a function of a linearly increasing voltage. Current is measured at two points for each pulse, the first point just before the pulse application and the second at the end of the pulse. This technique yields a curve with a peak that is directly proportional to species concentration. This allows for concentration discrimination of species in solution whose half-wave potential differs by as little as 40 to 50 mV.

$H_2S$ has an oxidation reaction at −0.14 V producing two electrons through $HS^-$ reaction with $Fe(CN)_6$ to yield the overall equation of: $H_2S \rightarrow S+2H^++2e^-$. Both CA and DPV can detect the electrons generated from $HS^-$ oxidation. And since both modalities are incorporated in contemporary potentiostats, both can be used for determining optimal electrochemical detection. During CA detection, the working electrode is fixed between −0.20-0.30 V to oxidize $H_2S/HS^-$, and during DPV a range of voltages is applied. The voltages for electron detection must sweep from −0.3 V to 0.3 V with a scan rate of 5-10 mV/sec and a scan increment 2-4 mV. An example of pulsing parameters are a pulse height of 25 mV, a step/drop time of 100 ms, and a pulse width of 50 ms; although these may vary by 50% depending on chip performance.

FIG. 4 illustrates one embodiment of working chamber conditions and electrochemical detection methodology. Electrochemical detection of $H_2S$ is performed in the three separate trapping chambers: the free sulfide trapping chamber 143; the acid labile sulfide trapping chamber 144; and the total sulfide trapping chamber 145. As explained above, the free sulfide reaction chamber 123 is preferably at neutral pH 7.0, the acid labile sulfide reaction chamber 124 at acid pH (pH from about 2.6 to about 6), and the total sulfide reaction chamber 125 at acid pH (pH from about 2.6 to about 6) plus 1 mM TCEP to liberate bound $H_2S$. Hydrogen sulfide gas will diffuse across the permeable membrane and be trapped in the corresponding trapping chambers due to the basic conditions present (pH from about 9.5 to about 10.0). FeCN will oxidize HS− to produce 2e−. The changes in electrochemical potential can be measured using a potentiostat coupled to the embedded electrodes. The potentiostat can be coupled to the integrated electrode systems 153, 154, 155, preferably via a copper wire that is adhered to the electrodes with a silver epoxy.

Fluorescence, Chemiluminescence and Colorimetric Detection

As depicted in FIG. 7, the hydrogen sulfide detecting apparatus 100 can alternatively feature a transparent base 151 to allow $H_2S$ levels in the trapping chambers 143, 144, 145 to be detected via fluorescence, chemiluminescence and colorimetric dyes. Dyes such as bimane compounds, including but not limited to dibromobimane, monobromobimane, benzodithiolone, and dansyl azide, can be used in conjunction with fluorescence excitation and emission spectrometry to detect sulphide. Hydrogen sulphide reaction with electron-poor aromatic or other electrophilic chemicals can produce color shifts in the visible light spectrum. For example nitrobenzofurazan thioether compounds can react to form nitrobenzofurazan thiol with a shift in absorbance spectrum at 534 nm. Hydrogen sulphide contained within the trapping chambers 143, 144, 145 can be detected by chemiluminescence through reaction with ozone or other electrophilic compounds to stimulate photon release.

Device Fabrication

A hydrogen sulfide detecting apparatus exemplifying the principles of the present invention can be fabricated utilizing a variety of materials and techniques. One preferred method is to fabricate in layers via PDMS. Alternate polymer materials, apart from PDMS may be utilized that include SU-8 polymers or similar structures. Additives to the base material may be employed, such as polyethylene oxide (PEO). These additives can increase the capillary action of the devices. Other methods include but are not limited to the use of silicon or metals such as copper. For example, a suitable microfabrication procedure would be to utilize bulk micro-machined silicon wafers that serve as the device substrate. Alternate fabrication processes may be utilized including layer-by-layer deposition through advanced printing and processing, but not limited to 3D printing. Casting via mold-and-pour could also be used to generate the appropriate structures given non-permeable materials.

In a preferred embodiment, the hydrogen sulfide detecting apparatus of the present invention is constructed in layers utilizing PDMS construction in combination with other polymer materials. For example, the hydrogen sulfide detecting apparatus 100 depicted in FIG. 2 is comprised of five layers. Referring to FIG. 2, the first layer 110 can comprise a butyl rubber cap 111. The second layer 120, which is bonded to the first layer 110, can be cast from a reusable mold to form the injection chamber 121, the plurality of reaction chambers 123, 124, 125, and inlet channels 122a-c. The third layer 130 can comprise a PDMS membrane 131 and is bonded to the second layer 120. The thickness of the membrane 131 may be varied depending on the material used and fabrication technology employed. The fourth layer 140 is bonded to the third layer 130 and comprises a plurality of trapping chambers 143, 144, 145 filled with a trapping buffer (e.g., 100 mM NaOH, pH from about 9.5 to about 10). In the preferred construction, the fourth layer 140 is a 1 mm thick section of PDMS that has trapping chambers 143, 144, 145 cut out of the PDMS material and aligned with the reaction chambers 123, 124, 125. The fifth layer 150 preferably consists of a plastic base 151 with interdigitated electrode systems 153, 154, 155 for electrochemical detection of the test specimen. The electrode systems 153, 154, 155 can be printed on the surface via microfabrication techniques and aligned with the trapping chambers 143, 144, 145 formed by cutouts in the fourth layer 140. The fifth layer 150 preferably is longer than the fourth layer 140, allowing access to the electrodes on the apparatus 100. For example, the first layer 110 can be 10 nm×2 nm, the second, third, and fourth layers 120, 130, 140 can be 40 nm×2.5 nm, and the fifth layer 150 can be 50 nm×2.5 nm. Other embodiments of the chip design could feature either increased or reduced dimensions to enable detection of larger or smaller volumes, respectfully. Finally, the fifth layer 150 is bonded to the fourth layer 140 and air is evacuated from the injection and releasing chambers.

FIG. 6 illustrates an exemplary process 200 for manufacturing the second layer 120 of the hydrogen sulfide detecting apparatus 100. In the preferred PDMS fabrication, a silicon nitride wafer is provided in step 201. In step 202, the silicon nitride wafer is spin-coated with 500 μm thick SU-8 photoresist and soft baked. Next, the wafer is exposed through a lithographic mask and baked post exposure (step 203). The photoresist is then developed and rinsed in step 204. In step 205, uncured PDMS is poured onto the mold and cured. In the preferred PDMS polymer construction, the cast is removed in step 206 and the injection chamber is cut out through the entire thickness of the cast in step 207. The required chemical reaction buffers for the acid labile (acid pH from about 2.6 to about 6.0) and total sulfide (acid pH plus 1 mM TCEP) can be coated by evaporation of concentrated solutions on to the surface of the respective chambers 124, 125 to complete the second layer 120. Final height of PDMS material should be high enough to encapsulate the designed channels with heights to 2000 microns. Design features include high surface areas consisting of, but not limited to, capillary channels that range from 1 to 400 microns in width with heights variable from 10 to 2000 microns. However, one skilled in the art will appreciate that channel height is determined based on required sample volumetric size. Additionally, one skilled in the art will recognize that the foregoing process may also be utilized for manufacturing the fourth layer 140 of the hydrogen sulfide detecting apparatus 100.

EXAMPLES

Example 1

The transfer efficiency of $H_2S$ across 75 μm and 150 μm PDMS membranes was demonstrated using an embodiment of a hydrogen sulfide detecting apparatus exemplifying the principles of the present invention. A sample was introduced into a single acid reaction chamber separated by a 75 μm PDMS membrane from an alkaline trapping chamber containing 10 mM monobromobimane (MBB). This experiment was repeated with a 150 μm PDMS membrane. The $H_2S$ transfer efficiency over time was measured by RP-HPLC detection of sulfide dibromane (SDB). FIG. 5 illustrates the diffusion of $H_2S$ across a PDMS membrane of different thicknesses, utilizing fluorescent detection by HPLC. The transfer efficiency of $H_2S$ from the acid reaction chamber into the trapping chamber is depicted as measured using a MBB detector for both a 75-μm membrane and a 150-μm membrane. The sodium sulfide volatilized the sulfide anion into $H_2S$ gas, which diffused across the membrane and was trapped in a separate chamber at pH 9.5 with 0.1 mM DTPA. Sample aliquots were taken from the trapping chamber at specified times. The amount of sulfide was detected using fluorescent HPLC analysis as described in PCT/US2013/031354, which is incorporated herein by reference. As shown in FIG. 5, an approximate 15% transfer efficiency occurred within 10 minutes using the 75-μm membrane, while an approximate 50% transfer efficiency occurred within 10 minutes using the 150-μm membrane. The transfer efficiency of $H_2S$ across the permeable membrane can be utilized to calibrate the hydrogen sulfide detecting apparatus 100.

Example 2

An embodiment of a hydrogen sulfide detecting apparatus exemplifying the principles of the present invention can be used to determine the concentration of $H_2S$ in a specimen using electrochemical, fluorescence, or colorimetric detection methods. In such instances, a blood sample will be obtained from a subject and placed into vacutainer tubes containing lithium heparin (BD Biosciences, Cat. No. 367886), which is then immediately centrifuged at 4° C. at 1500 RCF for 4 minutes to separate the plasma from the red blood cells. The plasma sample will then be injected into the injection chamber 121 of the apparatus 100 via a 26-gauge needle and 1 cc syringe. The sample will be pulled into the injection chamber 121 which is evacuated of air by wicking action, where it will be further pulled into the three parallel reaction chambers 123, 124, 125 for free sulfide, acid labile+free sulfide, and total sulfide detection respectively. The buffer components that coat the chambers will dissolve in the plasma sample, providing the correct pH and chemical concentrations necessary for the reactions to occur at room temperature. After approximately 15 minutes, hydrogen sulfide will be liberated from each of the reaction chambers 123, 124, 125; will diffuse across the membrane 130; and will be trapped in the alkaline buffer in the respective trapping chambers 143, 144, 145. Detection can then be accomplished by one of the three following methods: (a) electrochemical, (b) fluorescence, or (c) colorimetric.

If the electrochemical method is to be employed, the apparatus 100 will be connected to a potentiostat such as the VersaStat 4 (Princeton Applied Research), with one lead each for the working electrode, counter electrode, and reference electrode. A method such as differential pulse voltammetry (DPV) will be used to acquire a signal that is a measure of hydrogen sulfide concentration in the plasma sample. Typical settings for the DPV parameters are 25 mV for pulse height, 50 msec for pulse width, 1 mV for step height, and 100 msec for step width. Peak currents will be obtained for each chamber and converted into sulfide concentrations based on a calibration function (See Example 1).

If a fluorescence method is to be employed, the apparatus 100 will have a fluorescent dye such as dibromobimane (DBB) dissolved in solution in the trapping chambers 143, 144, 145. After reaction between dye and hydrogen sulfide in the trapping chambers 143, 144, 145, fluorescence will be measured using appropriate excitation and emission wavelengths. If DBB dye is used these are 358 nm and 484 nm respectively. Fluorescence will be quantified and converted to sulfide concentrations by means of a calibration function (See Example 1).

If a colorimetric method is to be used, the apparatus 100 will have a compound such as nitrobenzofurazan thioether dissolved in solution in the trapping chambers 143, 144, 145. Upon reaction with sulfide, it will form nitrobenzofurazan thiol, with a shift in the absorbance spectrum at 534 nm as previously noted. Absorbance will be quantified and converted to sulfide concentrations by means of a calibration function (See Example 1).

Free sulfide, acid-labile sulfide, bound sulfane sulfur, and total sulfide can then be calculated as follows. Free sulfide and total sulfide concentrations will be equal to that measured in the free sulfide and total sulfide trapping chambers 143, 145 respectively. The acid labile sulfide concentration will be equal to that measured in the "acid labile+free sulfide" chamber 144 minus the concentration in the free sulfide chamber 143. The bound sulfane sulfur concentration will be found by subtracting the concentration measured in the "acid labile+free sulfide" chamber 144 from that measured in the total sulfide chamber 145.

The foregoing description and accompanying drawings illustrate the principles, exemplary embodiments, and modes of operation of the invention. However, the invention should not be construed as being limited to the particular embodiments discussed above. Many modifications of the embodiments described herein will come to mind to one skilled in the art having the benefit of the teaching presented in the foregoing descriptions and the associated drawings. Accordingly, it should be appreciated that variations to those embodiments can be made by those skilled in the art without departing from the scope of the invention.

What is claimed is:
1. A hydrogen sulfide (H₂S) detecting apparatus comprising:
   a. an injection chamber;
   b. a plurality of reaction chambers in fluid communication with the injection chamber, wherein the plurality of reaction chambers comprise: a free sulfide reaction chamber; an acid labile sulfide reaction chamber; and a total sulfide reaction chamber;
   c. a plurality of trapping chambers positioned adjacent to the plurality of reaction chambers;
   d. a H₂S-permeable membrane positioned between the plurality of reaction chambers and the plurality of trapping chambers;
   wherein the plurality of reaction chambers define respective separate volumes from the injection chamber; and each of the reaction chambers are in fluid communication with the injection chamber.

2. The hydrogen sulfide detecting apparatus of claim 1, wherein the free sulfide reaction chamber has a neutral pH environment with a pH from about 7.0 to about 7.5.

3. The hydrogen sulfide detecting apparatus of claim 2, wherein the acid labile sulfide reaction chamber has an acidic environment with a pH from about 2.6 to about 6.0.

4. The hydrogen sulfide detecting apparatus of claim 3, wherein the total sulfide reaction chamber has an acidic environment with a pH from about 2.6 to about 6.0 and further comprises a reducing agent.

5. The hydrogen sulfide detecting apparatus of claim 4, wherein the reducing agent is selected from the group consisting of: tris(2-carboxyethyl)phosphine hydrochloride and dithiothreitol.

6. The hydrogen sulfide detecting apparatus of claim 4, wherein the plurality of trapping chambers comprise:
   a. a free sulfide trapping chamber positioned adjacent to the free sulfide reaction chamber such that such that H₂S gas released from the free sulfide reaction chamber will diffuse across the H₂S-permeable membrane and into the free sulfide trapping chamber;
   b. an acid labile sulfide trapping chamber positioned adjacent to the acid labile sulfide reaction chamber such that such that H₂S gas released from the acid labile sulfide reaction chamber will diffuse across the H₂S-permeable membrane and into the acid labile sulfide trapping chamber; and
   c. a total sulfide trapping chamber positioned adjacent to the total sulfide reaction chamber such that such that H₂S gas released from the total sulfide reaction chamber will diffuse across the H₂S-permeable membrane and into the total sulfide trapping chamber.

7. The hydrogen sulfide detecting apparatus of claim 6, wherein the plurality of trapping chambers each have an alkaline environment.

8. The hydrogen sulfide detecting apparatus of claim 6, wherein the plurality of trapping chambers each have an alkaline environment with a pH from about 9.5 to about 10.0.

9. The hydrogen sulfide detecting apparatus of claim 7, further comprising a base positioned adjacent to the plurality of trapping chambers.

10. The hydrogen sulfide detecting apparatus of claim 9, wherein the base comprises a plurality of electrode systems to enable electrochemical detection of H₂S in the adjacent plurality of trapping chambers.

11. The hydrogen sulfide detecting apparatus of claim 10, wherein the plurality of electrode systems comprise: a first electrode system positioned adjacent to the free sulfide trapping chamber; a second electrode system positioned adjacent to the acid labile sulfide trapping chamber; and a third electrode system positioned adjacent to the total sulfide trapping chamber.

12. The hydrogen sulfide detecting apparatus of claim 11, wherein the plurality of electrode systems each comprise a reference electrode, a counter electrode, and a working electrode.

13. The hydrogen sulfide detecting apparatus of claim 9, wherein the base is transparent to enable fluorimetric or colorimetric detection of H₂S in the adjacent plurality of trapping chambers.

14. The hydrogen sulfide detecting apparatus of claim 9, wherein the injection chamber is in fluid communication with the plurality of reaction chambers via a plurality of inlet channels, wherein the plurality of inlet channels comprise:
   a. A first inlet channel connecting the injection chamber to the free sulfide reaction chamber;
   b. a second inlet channel connecting the injection chamber to the acid labile sulfide reaction chamber; and
   c. a third inlet channel connecting the injection chamber to the total sulfide reaction chamber.

15. The hydrogen sulfide detecting apparatus of claim 14, further comprising a cap positioned adjacent to the injection chamber to allow a test sample to be injected through the cap and into the injection chamber.

16. A hydrogen sulfide (H₂S) detecting apparatus formed as a lab on a chip comprising:
   a. an injection chamber defined in the chip;
   b. a plurality of reaction chambers separately defined in the chip from the injection chamber and in fluid communication with the injection chamber, the plurality of reaction chambers comprising:
      i. a free sulfide reaction chamber having a pH from about 7.0 to about 7.5;
      ii. an acid labile sulfide reaction chamber having a pH from about 2.6 to about 6.0; and
      iii. a total sulfide reaction chamber having a pH from about 2.6 to about 6.0 and further having a reducing agent;
   c. a plurality of trapping chambers defined in the chip and fixedly positioned adjacent to the plurality of reaction chambers, wherein the plurality of trapping chambers each have an alkaline environment with a pH from about 9.5 to about 10.0;
   d. a H₂S-permeable membrane positioned directly between the plurality of reaction chambers and the plurality of trapping chambers; and
   e. a base positioned adjacent to the plurality of trapping chambers.

17. The hydrogen sulfide detecting apparatus of claim 16, wherein the plurality of trapping chambers comprise:
   a. a free sulfide trapping chamber positioned adjacent to the free sulfide reaction chamber such that such that H₂S gas released from the free sulfide reaction chamber will diffuse across the H₂S-permeable membrane and into the free sulfide trapping chamber;
   b. an acid labile sulfide trapping chamber positioned adjacent to the acid labile sulfide reaction chamber such that such that H₂S gas released from the acid labile sulfide reaction chamber will diffuse across the H₂S-permeable membrane and into the acid labile sulfide trapping chamber; and
   c. a total sulfide trapping chamber positioned adjacent to the total sulfide reaction chamber such that such that H₂S gas released from the total sulfide reaction chamber will diffuse across the H$_2$S-permeable membrane and into the total sulfide trapping chamber.

18. The hydrogen sulfide detecting apparatus of claim 17, wherein the base comprises a plurality of electrode systems to enable electrochemical detection of H$_2$S in the adjacent plurality of trapping chambers, wherein the plurality of electrode systems comprise: a first electrode system positioned adjacent to the free sulfide trapping chamber; a second electrode system positioned adjacent to the acid labile sulfide trapping chamber; and a third electrode system positioned adjacent to the total sulfide trapping chamber;

the plurality of electrode systems are formed as a chronoamperometry electrode system;

the base is fixedly attached to both the plurality of trapping chambers and the plurality of reaction chambers; and each reaction chamber includes interdigitated microchannels.

* * * * *